United States Patent [19]

Mitsushima et al.

[11] Patent Number: 5,338,676
[45] Date of Patent: Aug. 16, 1994

[54] CEPHALOSPORIN ACETYLHYDROLASE GENE AND PROTEIN ENCODED BY SAID GENE

[75] Inventors: Kenji Mitsushima, Osaka; Akio Takimoto, Kobe; Shigeo Yaqi, Takatsuki; Takayasu Sonoyama, Sakai, all of Japan

[73] Assignee: Shionogi & Co., Ltd., Osaka, Japan

[21] Appl. No.: 980,517

[22] Filed: Nov. 25, 1992

Related U.S. Application Data

[62] Division of Ser. No. 688,299, Apr. 22, 1991.

[30] Foreign Application Priority Data

Apr. 27, 1990 [JP] Japan ................. 2-113483

[51] Int. Cl.$^5$ .................. C12N 9/18; C12N 15/00
[52] U.S. Cl. .................... 435/197; 536/23.2
[58] Field of Search ............ 435/197, 172.3, 320.1, 435/252.33; 536/23.2

[56] References Cited

U.S. PATENT DOCUMENTS 3,304,236 2/1967 Nuesch et al.

FOREIGN PATENT DOCUMENTS 0322032 6/1989 European Pat. Off.
8015926 6/1981 France.
49-132294 12/1974 Japan.
59-108790 6/1984 Japan.
61-67489 4/1986 Japan.

OTHER PUBLICATIONS

Konecny et al., Biochimica et Biophysica Acta, vol. 485 (1977) pp. 367–378.
Higerd et al., Journal of Bacteriology, vol. 114, No. 3 1977 pp. 1184–1192.
J. Konecny, Enzymatic Deacetylation of Cephalosporins pp. 253–259.
Abbott et al, Applied Microbiology, vol. 20, No. 3, pp. 413–419 (1975).
Abbott et al, Methods in Enzymology, vol. 43, pp. 731–734 (1975).
Suggs et al. *PNAS*, vol. 78, No. 11, Nov. 1981, pp. 6613–6617.

*Primary Examiner*—Robert A. Wax
*Assistant Examiner*—Keith D. Hendricks
*Attorney, Agent, or Firm*—Birch, Stewart, Kolasch & Birch

[57] ABSTRACT

A cephalosporin acetylhydrolase gene, a recombinant DNA molecule prepared by introducing said gene into a vector used in an *E. coli* host-vector system, *E. coli* cells transfomed with said recombinant DNA molecule, a protein having the amino acid sequence encoded by said gene, an enzyme which is a multimer of said protein, and a process for preparing said protein or enzyme are provided, said cephalosporin acetylhydrolase being an enzyme useful for converting cephalosporins such as cephalosporin C and 7-ACA into deacetylated ones such as deacetylcephalosporin C and deacetyl 7-ACA which are useful as an intermediate for preparing a variety of derivatized cephalosporin antibiotics.

12 Claims, 12 Drawing Sheets

Fig. 1

Gln-Leu-Phe-Asp-Leu-Pro-Leu-Asp-Gln-Leu-Gln-
Thr-Tyr-Lys-Pro-Glu-Lys-Thr-Ala-Pro-Lys-Asp-Phe-
Ser-Glu-Phe-Trp-Lys-Leu-Ser-Leu-Glu-Glu-Leu-Ala-
Lys-Val-Gln-Ala-Glu-Pro-Asp-Leu-Gln-Pro-Val-Asp-
Tyr-Pro-Ala-Asp-Gly-Val-Lys-Val-Tyr-Arg-Leu-Thr-
Tyr-Lys-Ser-Phe-Gly-Asn-Ala-Arg-Ile-Thr-Gly-Trp-
Tyr-Ala-Val-Pro-Asp-Lys-Gln-Gly-Pro-His-Pro-Ala-
Ile-Val-Lys-Tyr-His-Gly-Tyr-Asn-Ala-Ser-Tyr-Asp-
Gly-Glu-Ile-His-Glu-Met-Val-Asn-Trp-Ala-Leu-His-
Gly-Tyr-Ala-Ala-Phe-Gly-Met-Leu-Val-Arg-Gly-Gln-
Gln-Ser-Ser-Glu-Asp-Thr-Ser-Ile-Ser-Leu-His-Gly-His-
Ala-Leu-Gly-Trp-Met-Thr-Lys-Gly-Ile-Leu-Asp-Lys-
Asp-Thr-Tyr-Tyr-Tyr-Arg-Gly-Val-Tyr-Leu-Asp-Ala-
Val-Arg-Ala-Leu-Glu-Val-Ile-Ser-Ser-Phe-Asp-Glu-
Val-Asp-Glu-Thr-Arg-Ile-Gly-Val-Thr-Gly-Gly-Ser-
Gln-Gly-Gly-Gly-Leu-Thr-Ile-Ala-Ala-Ala-Ala-Leu-
Ser-Asp-Ile-Pro-Lys-Ala-Ala-Val-Ala-Asp-Tyr-Pro-
Tyr-Leu-Ser-Asn-Phe-Glu-Arg-Ala-Ile-Asp-Val-Ala-
Leu-Glu-Gln-Pro-Tyr-Leu-Glu-Ile-Asn-Ser-Phe-Phe-
Arg-Arg-Asn-Gly-Ser-Pro-Glu-Thr-Glu-Val-Gln-Ala-
Met-Lys-Thr-Leu-Ser-Tyr-Phe-Asp-Ile-Met-Asn-Leu-
Ala-Asp-Arg-Val-Lys-Val-Pro-Val-Leu-Met-Ser-Ile-
Gly-Leu-Ile-Asp-Lys-Val-Thr-Pro-Pro-Ser-Thr-Val-
Phe-Ala-Ala-Tyr-Asn-His-Leu-Glu-Thr-Glu-Lys-Glu-
Leu-Lys-Val-Tyr-Arg-Tyr-Phe-Gly-His-Glu-Tyr-Ile-
Pro-Ala-Phe-Gln-Thr-Glu-Lys-Leu-Ala-Phe-Phe-Lys-
Gln-His-Leu-Lys-Gly

Fig. 2a

```
  1    Met Gln Leu Phe Asp Leu Pro Leu Asp Gln   10
  1    ATG CAA CTA TTC GAT CTG CCG CTC GAC CAA   30

11    Leu Gln Thr Tyr Lys Pro Glu Lys Thr Ala   20
 31    TTG CAA ACA TAT AAG CCT GAA AAA ACA GCA   60

21    Pro Lys Asp Phe Ser Glu Phe Trp Lys Leu   30
 61    CCG AAA GAT TTT TCT GAG TTT TGG AAA TTG   90

31    Ser Leu Glu Glu Leu Ala Lys Val Gln Ala   40
 91    TCT TTG GAG GAA CTT GCA AAA GTC CAA GCA  120

41    Glu Pro Asp Leu Gln Pro Val Asp Tyr Pro   50
121    GAA CCT GAT CTA CAG CCG GTT GAC TAT CCT  150

51    Ala Asp Gly Val Lys Val Tyr Arg Leu Thr   60
151    GCT GAC GGA GTA AAA GTG TAC CGT CTC ACA  180

61    Tyr Lys Ser Phe Gly Asn Ala Arg Ile Thr   70
181    TAT AAA AGC TTC GGA AAC GCC CGC ATT ACC  210

71    Gly Trp Tyr Ala Val Pro Asp Lys Gln Gly   80
211    GGA TGG TAC GCG GTG CCT GAC AAG CAA GGC  240

81    Pro His Pro Ala Ile Val Lys Tyr His Gly   90
241    CCG CAT CCG GCG ATC GTG AAA TAT CAT GGC  270

91    Tyr Asn Ala Ser Tyr Asp Gly Glu Ile His  100
271    TAC AAT GCA AGC TAT GAT GGT GAG ATT CAT  300

101    Glu Met Val Asn Trp Ala Leu His Gly Tyr  110
301    GAA ATG GTA AAC TGG GCA CTC CAT GGC TAC  330

111    Ala Ala Phe Gly Met Leu Val Arg Gly Gln  120
331    GCC GCA TTC GGC ATG CTT GTC CGC GGC CAG  360

121    Gln Ser Ser Glu Asp Thr Ser Ile Ser Leu  130
361    CAG AGC AGC GAG GAT ACG AGT ATT TCA CTG  390

131    His Gly His Ala Leu Gly Trp Met Thr Lys  140
391    CAC GGT CAT GCT TTG GGC TGG ATG ACG AAA  420

141    Gly Ile Leu Asp Lys Asp Thr Tyr Tyr Tyr  150
421    GGA ATT CTT GAT AAA GAT ACA TAC TAT TAC  450

151    Arg Gly Val Tyr Leu Asp Ala Val Arg Ala  160
451    CGC GGT GTT TAT TTG GAC GCC GTC CGC GCG  480

161    Leu Glu Val Ile Ser Ser Phe Asp Glu Val  170
481    CTT GAG GTC ATC AGC AGC TTC GAC GAG GTT  510
```

Fig. 2b

```
171  Asp Glu Thr Arg Ile Gly Val Thr Gly Gly  180
511  GAC GAA ACA AGG ATC GGT GTG ACA GGA GGA  540

181  Ser Gln Gly Gly Gly Leu Thr Ile Ala Ala  190
541  AGC CAA GGC GGA GGT TTA ACC ATT GCC GCA  570

191  Ala Ala Leu Ser Asp Ile Pro Lys Ala Ala  200
571  GCA GCG CTG TCA GAC ATT CCA AAA GCC GCG  600

201  Val Ala Asp Tyr Pro Tyr Leu Ser Asn Phe  210
601  GTT GCC GAT TAT CCT TAT TTA AGC AAC TTC  630

211  Glu Arg Ala Ile Asp Val Ala Leu Glu Gln  220
631  GAA CGG GCC ATT GAT GTG GCG CTT GAA CAG  660

221  Pro Tyr Leu Glu Ile Asn Ser Phe Phe Arg  230
661  CCG TAC CTT GAA ATC AAT TCC TTC TTC AGA  690

231  Arg Asn Gly Ser Pro Glu Thr Glu Val Gln  240
691  AGA AAT GGC AGC CCG GAA ACA GAA GTG CAG  720

241  Ala Met Lys Thr Leu Ser Tyr Phe Asp Ile  250
721  GCG ATG AAG ACA CTT TCA TAT TTC GAT ATT  750

251  Met Asn Leu Ala Asp Arg Val Lys Val Pro  260
751  ATG AAT CTC GCT GAC CGA GTG AAG GTG CCT  780

261  Val Leu Met Ser Ile Gly Leu Ile Asp Lys  270
781  GTC CTG ATG TCA ATC GGC CTG ATT GAC AAG  810

271  Val Thr Pro Pro Ser Thr Val Phe Ala Ala  280
811  GTC ACG CCG CCG TCC ACC GTG TTT GCC GCC  840

281  Tyr Asn His Leu Glu Thr Glu Lys Glu Leu  290
841  TAC AAT CAT TTG GAA ACA GAG AAA GAG CTG  870

291  Lys Val Tyr Arg Tyr Phe Gly His Glu Tyr  300
871  AAG GTG TAC CGC TAC TTC GGA CAT GAG TAT  900

301  Ile Pro Ala Phe Gln Thr Glu Lys Leu Ala  310
901  ATC CCT GCT TTT CAA ACG GAA AAA CTT GCT  930

311  Phe Phe Lys Gln His Leu Lys Gly ***
931  TTC TTT AAG CAG CAT CTT AAA GGC TGA
```

Fig. 3

Tyr-His-Gly-Tyr-Asn-Ala-Ser-Tyr-Asp-Gly-

Glu-Ile-His-<u>Glu-Met-Val-Asn-Trp-Ala</u>-Leu-

His-Gly-Tyr-Ala-Ala-Phe-Gly-Met-Leu-Val-

X -Gly-Gln-Gln-

Fig. 4

| amino acid sequence | -Glu-Met-Val-Asn-Trp-Ala |
|---|---|
| base sequence | ```
                T
       G     A  T
5'- GA ATG GT AA TGG GC -3'
    A     C  C
          G A
    C  T  A
3'- CT TAC CA TT ACC CG -5'
    T     G  G
             C
``` |
| synthetic probe | |
| CAH-RM1 | 3'  CT  TAC  CAA  TT  ACC  CG  5' (with C/T above first CAA position and A/G above) |
| CAH-RM2 | 3'  CT  TAC  CAT  TT  ACC  CG  5' |
| CAH-RM3 | 3'  CT  TAC  CAG  TT  ACC  CG  5' |
| CAH-RM4 | 3'  CT  TAC  CAC  TT  ACC  CG  5' |

☐ inserted DNA fragment (from B. subtilis FERM BP-2755)

— pUC13

◀ position at which probe is hybridized

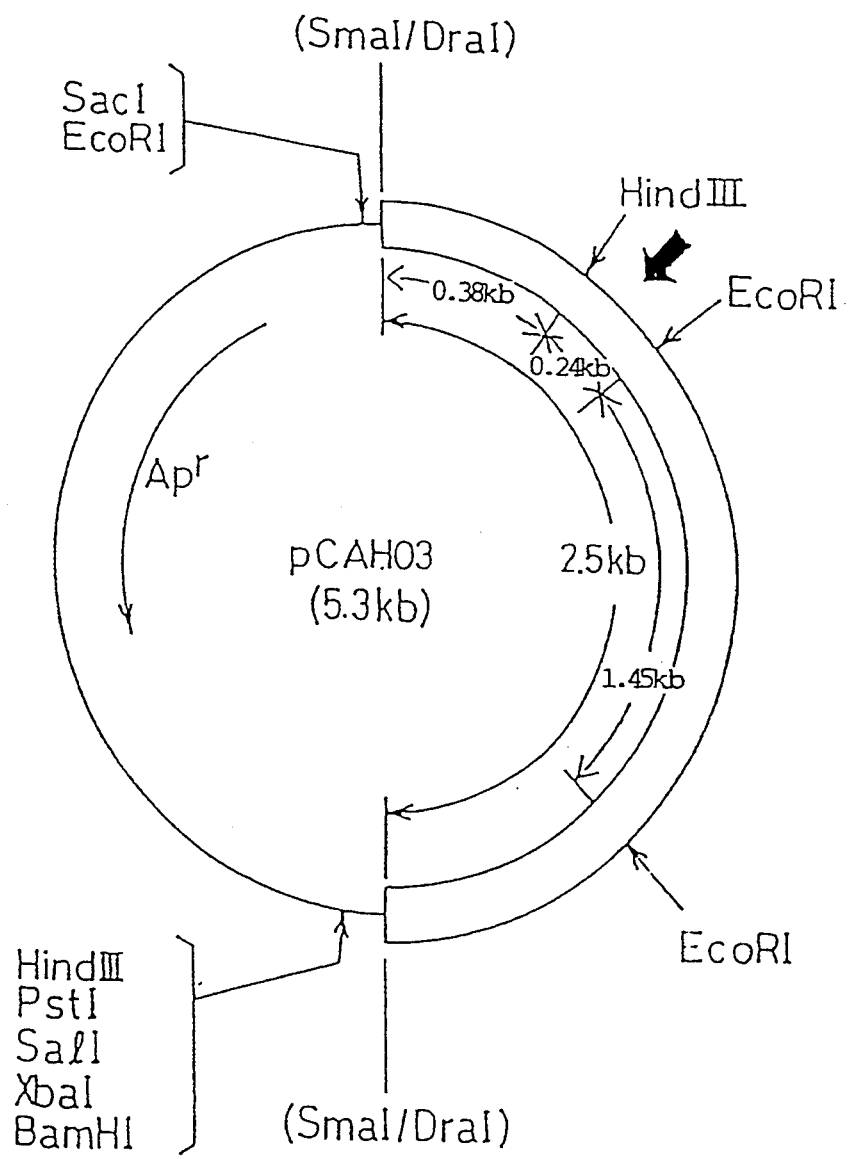

Fig. 7a

```
         10        20        30        40        50        60        70        80        90
(DraI)
AAAGAACCGCTATGTCAGTCTGACGGGCCCAGGCCTTTATGGAACTAAGCCGGGAAAGTCTTAAACAACGTTTGATGAAGGCTGTCTGGG

AAACAAAGATGAAATATTTAGAAAACAAGACGAAAGTGGTAGTATAGGAATACAAACTAAATCTTATAAACAAAGGGAATAATCG

GAAATGCAACTATTCGATCTGCCGCTCGACCAATTGCAAACATATAAGCCTGAAAAAACAGCACCGAAAGATTTTCTGAGTTTTGGAAA
        MetGlnLeuPheAspLeuProLeuAspGlnLeuGlnThrTyrLysProGluLysThrAlaProLysAspPheSerGluPheTrpLys

TTGTCTTTGGAGGAACTTGCAAAAGTCGAAAGTCCAAGCAGAACCTGATCTACAGCCGGTTGACTATCCTGCTGACGGAGTAAAAGTACCGTCTC
LeuSerLeuGluGluLeuAlaLysValGlnAlaAspLeuGlnProValAspTyrProAlaAspGlyValLysValTyrArgLeu

ACATATAAAAGCTTCCGAAACGCCCGCATTACCGGATGGTACCGGTGCCTGACAAGCAAGCCCGCATCGGCGATCGTGAAATATCAT
ThrTyrLysSerPheGlyAsnAlaArgIleThrGlyTyrArgValProAspLysGlnGlyProHisProAlaIleValLysTyrHis

GGCTACAATGCAAGCTATGATGGTGAGATTCATGAAATGTAAACTGGGCACTCCATGCTACGCCCGCATTCGGCATGCTTGTCCGCGGC
GlyTyrAsnAlaSerTyrAspGlyGluIleHisGluMetValAsnTrpAlaLeuHisGlyTyrAlaAlaPheGlyMetLeuValArgGly

CAGCAGCAGGATACGAGGATACGAGTATTCACTGCAGTAGTATTTGGGCTGATGACGAAAGGAATTCTTGATAAAGATACATACTAT
GlnGlnSerSerGluAspThrSerIleSerLeuHisGlyHisAlaLeuGlyTrpMetThrLysGlyIleLeuAspLysAspThrTyrTyr

TACCGGGTGTTTATTTGGACGCCGCTCCGCGGTTGAGGTCATCAGCGAGCTTGACGAGTTGACGAAACAAGGATCGGTGTGACAGGA
TyrArgGlyValPheIleTrpThrProLeuGluValIleSerGluLeuAspGluValAspGluLeuThrArgIleGlyValThrGly

GGAAGCCAAGCGGAGGTTTAACCATTGCCGCAGCAGCAGCCCGTTGCCGCAGCATTCCAAAAGCCGTTGCCGCGATTATCCTTATTAAGCAAC
GlySerGlnGlyGlyGlyLeuThrIleAlaAlaAlaLeuGluGlnProLysAlaAlaLeuProLysAlaLeuAlaAspTyrProTyrLeuSerAsn

TTCGAACGGGCCATTGATGTGGCGCTTAACAGCCGTACCTTGAAATCAATTCCTTCTTCAGAAGAAATGGCAGCCCGGAAACAGAAGTG
PheGluArgAlaIleAspValAlaLeuGluGlnProTyrLeuGluIleAsnSerPheArgArgAsnGlySerProGluThrGluVal

CAGGCGATGAAGACACTTTCATATTTCGATATTATGAATCTCGCCTGATGTCCTGATGTCAATCGGCCCTGATTGAC
GlnAlaMetLysThrLeuSerTyrPheAspIleMetAsnLeuAlaAspArgValLysValProValLeuMetSerIleGlyLeuIleAsp
```

Fig. 7b

```
AAGGTCACGCCGCCGTCCACCGTGTTGCCGCCTACAATCATTTGGAAACAGAGAAAGAGCTGAAGGTGTACCGCTACTTCGGACATGAG
LysValThrProProSerThrValPheAlaAlaTyrAsnHisLeuGluThrGluLysGluLeuLysValTyrArgTyrPheGlyHisGlu

TATATCCCTGCTTTTCAAACGGAAAAACTTGCTTTCTTTAAGCAGCATCTTAAAGGCTGATAAATGTGAAAAGCCCGCCATATCATCAG
TyrIleProAlaPheGlnThrGluLysLeuAlaPhePheLysGlnHisLeuLysGly***

GCGGTTTTTTCTGCAAACTGCCCGGAATGAGAACAGACTGAGAACAGAATATGAAACAAAGAATCATTAATGAATTAAAACGGATCG
AGCAGTCATACGGAGTCAAAATCGTGTATGCCGTCGAGTCAGGAAGCCCATGGAGAAGTTCCCTCGCAGGATAGTGATTACGACGTCC
GCTTTATTTATGTGCCGAAAAAGGAGTGGTACTTTTCGGCTTTCAATTGAGGTCGTGATGTCATTGAGGAACCGATTCACGATTTGCTGGATA
TCAGCGGCTGGGAGCTGAGAAAACGCTTCGGCTTTTCAAAAAGTCAAACCCTCCGCTCGTCCTCGAATGGCTGTCCTCAGACATTGTGTATT
ACGAAGCATTTACGACCCGAGACGCAGTTAAGAAAACTGCCACGGAGGCATTTAAGCCTGACAAGCGTGTATCACTACTATATCAATATGG
CGAGAAGGAACGTCAAAGATTATCCAAGGACAAGAGGTCAAAATTAAAAGTACTTCTACGTTCTTCGGCCTATTTTGGCTGCAATGG
ATTGAAAGCACGGAACCATACCGCCAATGGACTTTACTGTTTTGATGAATGAACTTGTGCTGAACCCGAGCTGAAGGCTGAAATGGAAA
CCTTGCTTGAACGGAAGGAAGAGAGGGAAGAACTGACCCTCGAATCAAAGAACTGATGTAATTCACCAATTCATTGAAACGAAATCGAA
AGAATCATGGAAGCGAACGACACAAAAAGAACTGAAGGCAGAGAAAAAGATATGACATCGAATTGAACCGTTTACTTTTGAATACGGTTGAAGAA
GTGTGGAAGGATGGAGGAAGCTGATGTTTTTTGTCGCTTCCTTCCTTTCTCCTTTATTCGACAGAATTC
                                                              EcoRI
```

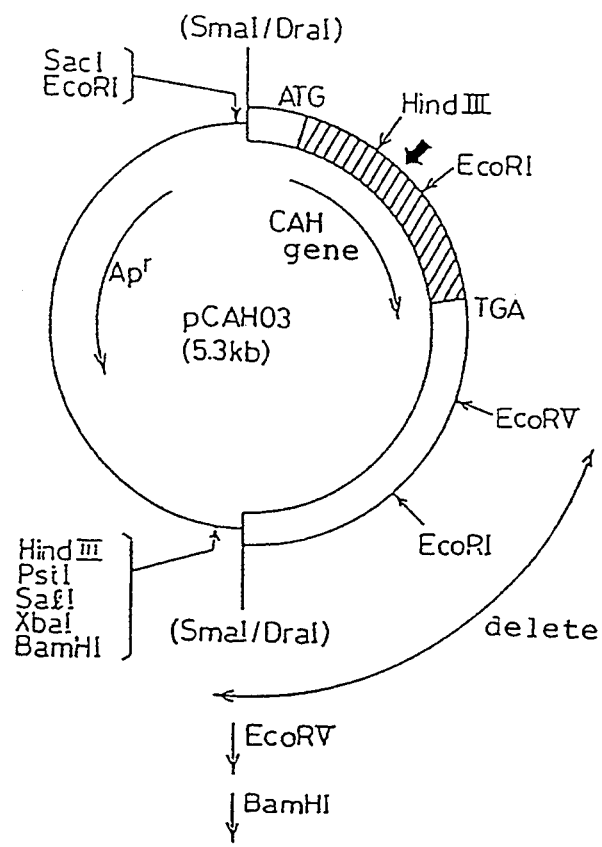
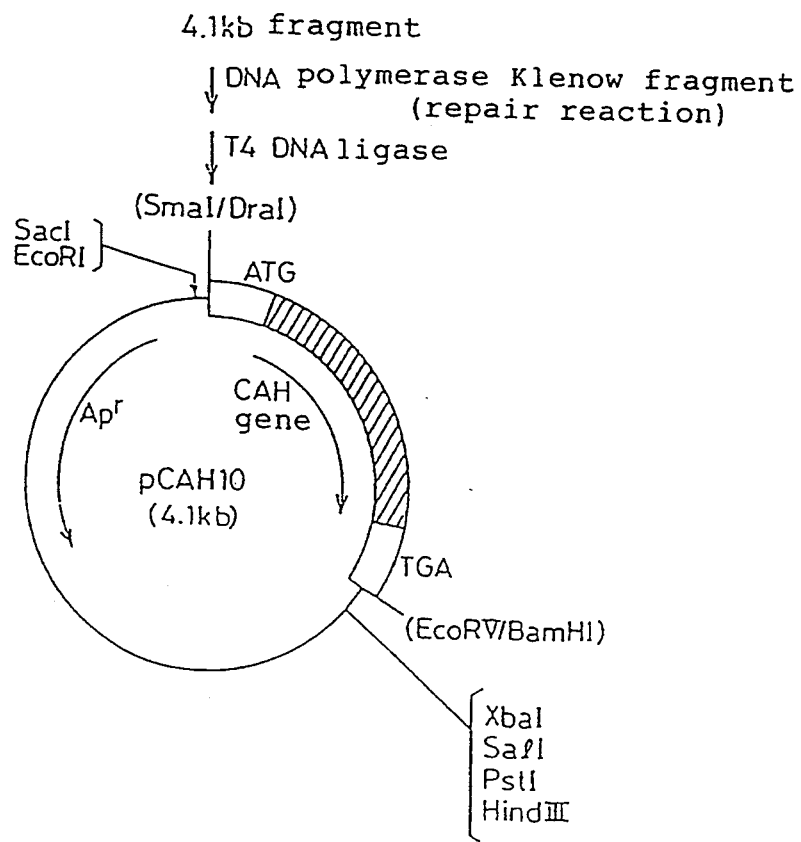
Fig. 8

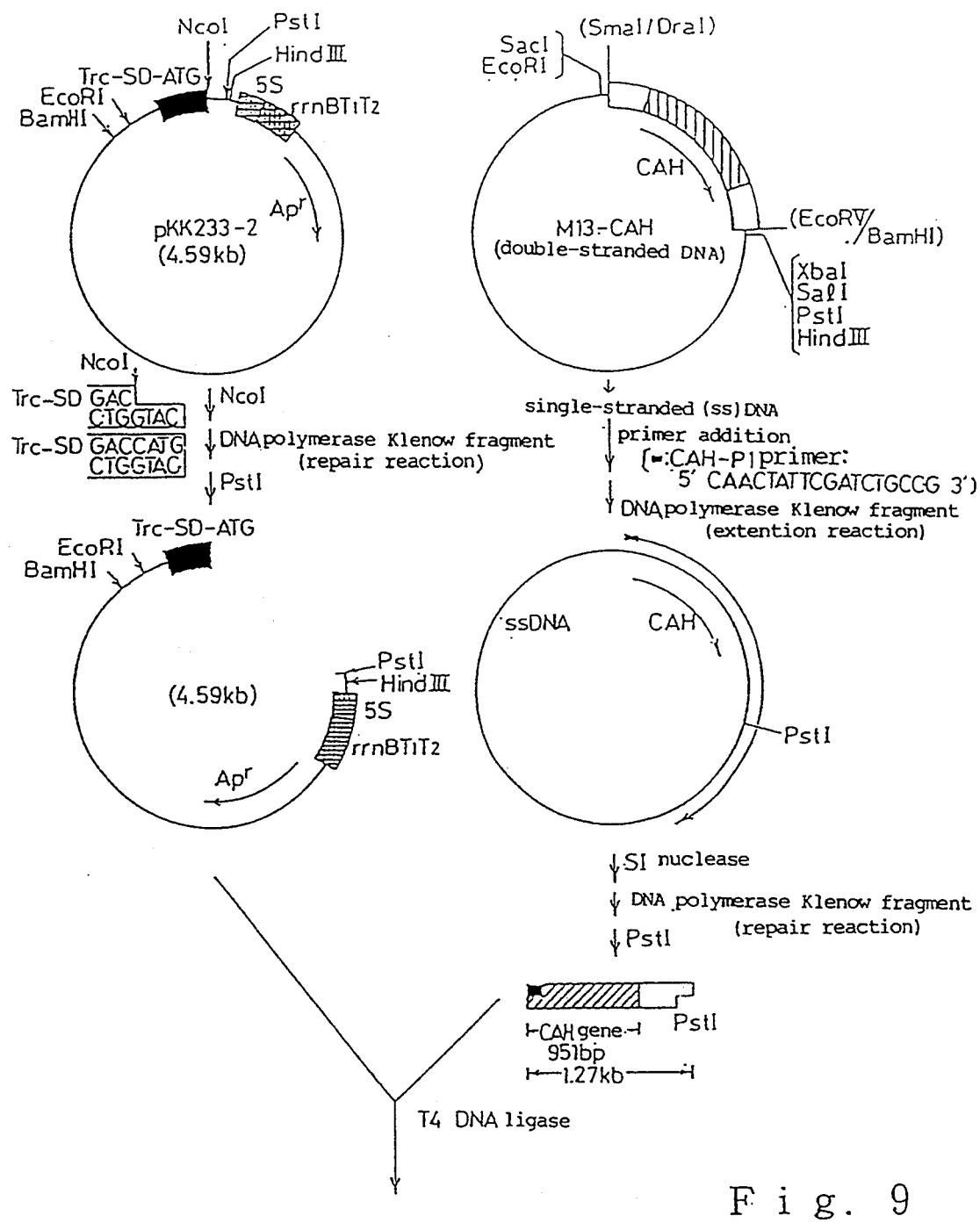
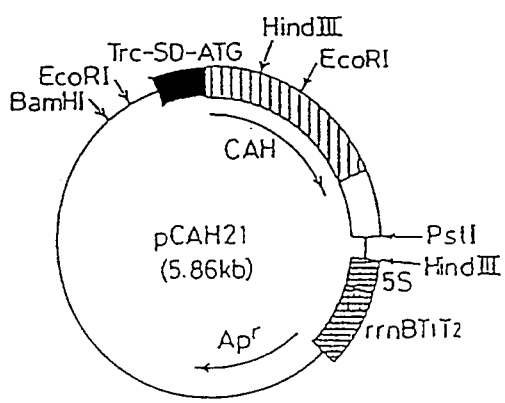
Fig. 9

CEPHALOSPORIN ACETYLHYDROLASE GENE AND PROTEIN ENCODED BY SAID GENE

This application is a divisional of copending application Ser. No. 07/688,299, filed on Apr. 22, 1991, the entire contents of which are hereby incorporated by reference

FIELD OF THE INVENTION

The present invention relates to a cephalosporin acetylhydrolase gene, a recombinant DNA molecule prepared by introducing said gene into a vector used in an *Escherichia coli* host-vector system, *E. coli* cells transformed with said recombinant DNA molecule, a protein having an amino acid sequence encoded by said gene, an enzyme comprising a multimer, preferably tetramer or octamer, of said protein, and a process for preparing said protein or enzyme.

PRIOR ART

Cephalosporins such as cephalosporin C and 7-aminocephalosporanic acid (hereafter referred to as 7-ACA) were hitherto derived by eliminating the acetyl group bonded to the hydroxymethyl group at their 3-position (hereafter referred to as deacetylation) to deacetylated compounds, such as deacetylcephalosporin C and deacetyl 7-ACA, which are useful as starting materials to synthesize a variety of cephalosporin antibiotics including those already on the market.

As a method for deacetylation of cephalosporins, there exist chemical and enzymatic methods. Of these methods, the latter is believed to be advantageous partly because it can be performed at an approximately neutral pH and at mild temperature and partly because it accompanies less side reaction. Several enzymatic methods have been already disclosed (for example, Japanese Patent Publication Nos. 108,790/1984, 132,294/1974 and 67,489/1986, and U.S. Pat. No. 3,304,236).

BRIEF DESCRIPTION OF THE INVENTION

The present inventors have found that a strain of *Bacillus subtilis* isolated from soil produces cephalosporin acetylhydrolase and efficiently produces deacetylcephalosporins by deacetylation of cephalosporins. This finding has led the inventors to the idea that the construction of a microorganism capable of preferentially producing the cephalosporin acetylhydrolase by recombinant DNA technology would be industrially very advantageous for preparing deacetylcephalosporins. Such a microorganism remarkably producing only cephalosporin acetylhydrolase is not known so far.

The present inventors have made an extensive study and succeeded in isolating a DNA fragment carrying a cephalosporin acetylhydrolase gene from *B. subtills* newly isolated from soil and in cloning of said DNA fragment in *E. coli.* They also found that *E. coli* transformed with a plasmid vector, into which said DNA fragment had been inserted, produced a remarkable amount of cephalosporin acetylhydrolase. The present invention has been completed on the basis of the above findings.

Thus, the present invention provides a cephalosporin acetylhydrolase gene, a recombinant DNA molecule containing said gene, *E. coli* cells transformed with said recombinant DNA molecule, a protein having an amino acid sequence encoded by said gene, an enzyme comprising a multimer of said protein, and a process for preparing said protein or enzyme.

The newly isolated strain, *Bacillus subtilis* SHS0133, from which the cephalosporin acetylhydrolase gene was obtained according to the present invention, was deposited at the Fermentation Research Institute, Agency of Industrial Science and Technology, 1-3, Higashi 1 chome, Tsukuba-shi, Ibaraki-ken, 305, Japan under Budapest Treaty with the accession number FERM BP-2755 (Date: Feb. 15, 1990).

BRIEF DESCRIPTION OF THE DRAWINGS

FIG. 1 depicts the amino acid sequence of cephalosporin acetylhydrolase (SEQ. ID. NO. 1).

FIGS. 2a and 2b depicts the base sequence of cephalosporin acetylhydrolase gene, (the lower row) (SEQ. ID. NO. 2) and the amino acid sequence deduced therefrom (the upper row) (SEQ. ID. NO. 2).

FIG. 3 depicts the partially determined amino acid sequence (34 amino acid residues) of cephalosporin acetylhydrolase (SEQ. ID. NO. 3).

FIG. 4 depicts four synthetic oligonucleotide probes including all of the genetically possible DNA base sequences deduced from the underlined amino acid sequence in FIG. 3.

FIG. 6 depicts the restriction enzyme cleavage map of recombinant plasmid pCAH03.

FIGS. 7a and 7b depicts the DNA sequence of the cloned cephalosporin acetylhydrolase gene and flanking regions (the upper row) (SEQ. ID. NO. 11) and the amino acid sequence deduced therefrom (the lower row) (SEQ. ID. NO. 11).

FIG. 8 depicts the construction of miniaturized plasmid pCAH10 which corresponds to plasmid pCAH03 but deletes a region downstream of cephalosporin acetylhydrolase gene.

FIG. 9 depicts the construction of expression plasmid pCAH21 used in *E. coli.*

DETAILED DESCRIPTION OF THE INVENTION

Characteristics of B. subtilis SHS0133

Figure 5:
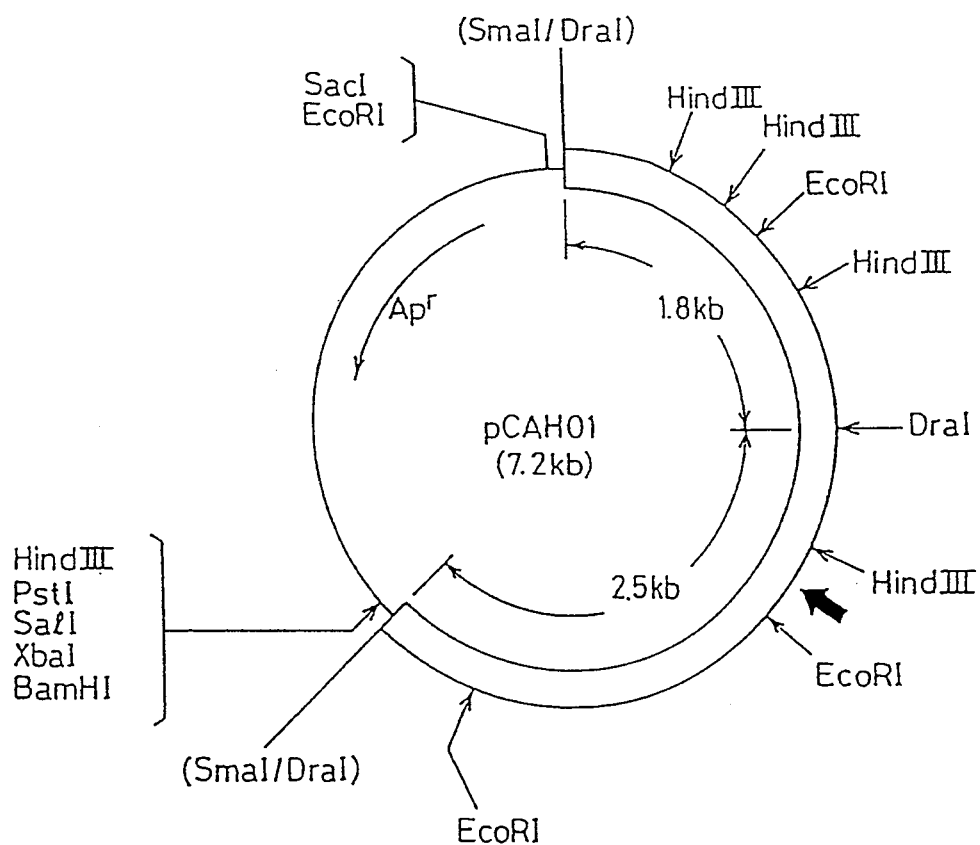
FIG. 5 depicts the restriction enzyme cleavage map of recombinant plasmid pCAH01 and the position at which the DNA probe hybridizes.

1. G+C mole percent(%) of chromosomal DNA: 43.4

2. Morphological characteristics

The strain is a gram-positive, short rod-shaped bacterium of $0.7-0.8 \times 1.8-2.6$ μm in size, and is peritrichous. This strain grows well under an aerobic condition and also grows weakly in a natural medium containing glucose under an anaerobic condition. Spore, $0.8 \times 1.3-1.7$ μm in size, is formed in the central part of the cell.

3. Cultural characteristics (1) Meat extract agar plate culture (at 30° C., for 7 days)

Colony formation: 24 hours after inoculation
Shape: irregular
Surface: gilled
Margin: undulate
Elevation: convex
Color: cream
Luster: dull
Optical property: opaque (2) Meat extract agar slant culture (at 30° C., for 7 days)
Growth: good
Shape: filiform
Surface: gilled
Color: cream
Luster: dull
Optical property: opaque
Consistency: butyrous
(3) Meat extract broth culture (at 30° C., for 7 days)
Growth on surface: thick film is formed
Clouding: slight
Odor: slightly aromatic
Sediment: visid
Amount of sediment: scanty
(4) Meat extract gelatin stab culture (at 24° C., for 30 days)
Growth: grows uniformly along the stab line
Line of puncture: filiform
Mode of liquefaction: liquefied on 7th day at 24° C. to form 0.5 mm of liquefied layer (stratiform)
(5) Litmus milk culture
Litmus is reduced. Casein is digested rapidly without coagulation.
4. Biochemical characteristics
(1) Reduction of nitrate: positive
(2) Denitrification: positive
(3) MR test: negative
(4) VP test: positive
(5) Formation of indole: negative
(6) Formation of $H_2S$:
   lead acetate paper: negative
   TSI: negative
   Krigler: negative
(7) Hydrolysis of starch: positive
(8) Utilization of citrate:
   Koser: positive
   Christensen: positive
(9) Utilization of inorganic nitrogen source:
   nitrate: positive
   ammonium: positive
(10) Formation of pigment: brown pigment was formed
(11) Urease test: positive
(12) Oxidase test: positive
(13) Catalase test: positive
(14) pH:
   growth range: 1.5–8.8
   optimum: 6.0–8.8
(15) Temperature:
   growth range: 16.5° C.–50.5° C.
   optimum: 26.0° C.–36.0° C.
(16) OF test:
   D-glucose: produces acids fermentatively without generating gas
   lactose: produces acids fermentatively without generating gas
(17) Formation of acids and gas from sugars:
   i) produces acids and no gas from L-arabinose, D-xylose, D-glucose, D-mannose, D-fructose, maltose, sucrose, trehalose, D-mannitol, glycerol, and starch;
   ii) produces neither acids nor gas from D-galactose, lactose, D-sorbitol, and inositol.
(18) Nutritional requirement: none
(19) Degradation of pectin: positive
(20) Degradation of hippuric acid: negative
(21) Formation of levan (from sucrose, raffinose): positive
(22) Arginine hydrolase: negative
(23) Lecithinase: negative
(24) Growth under anaerobic condition: grows weakly in natural medium containing D-glucose.

From the above results, the strain was identified to be one strain of *B. subtilis* on the basis of Bergey's Manual of Systematic Bacteriology, Vol. II, 1986, and designated as *Bacillus subtilis* SHS0133.

The present invention encompasses a process for preparing cephalosporin acetylhydrolase using a recombinant microorganism transformed with a recombinant DNA molecule prepared by introducing into a vector used in an *E. coli* host-vector system an isolated DNA base sequence encoding the amino acid sequence depicted in FIG. 1, preferably the DNA base sequence depicted in FIG. 2. This process may be realized by following the next seven steps which represent the history of the development of the present invention, although the process can be achieved by more simple procedure because of the reason that the DNA base sequence encoding the cephalosporin acetylhydrolase is revealed by this invention.

(1) *Bacillus subtills* (FERM BP-2755) is cultured in an appropriate medium and allowed to produce cephalosporin acetylhydrolase, and the produced cephalosporin acetylhydrolase is separated from the medium and purified. The purified enzyme is digested with an appropriate protease used in fragmentation of a protein, the resultant peptide fragments are separated, and then the amino acid sequence of one of the peptide fragments is determined from the amino terminus.

(2) Possible DNA base sequences corresponding to a part of the amino acid sequence determined are deduced, and a pool of oligonucleotides having the deduced base sequences are chemically synthesized, and the 5'-terminus of the oligonucleotides was labeled with $^{32}P$. The labeled oligonucleotides are used as probes for gene cloning.

(3) Chromosomal DNA is extracted and purified from *B. subtilis* (FERM BP-2755), digested with various restriction enzymes, electrophoresed on agarose gel, and the separated DNA fragments are transferred onto nitrocellulose membrane from the gel. Southern hybridization is then conducted using the nitrocellulose membrane and the $^{32}P$-labeled probes prepared in the above step (2) to select DNA fragments showing homology to the probes. Of the DNA fragments, a somewhat larger fragment as compared with the size of the desired gene expected from the molecular weight of cephalosporin acetylhydrolase protein is selected, relevant region on agarose gel containing the DNA fragment is excised, and the DNA is extracted.

(4) The DNA fragment from the above step (3) is inserted into an *E. coli* cloning vector and the resultant recombinant plasmid is introduced into *E. coli* cells by transformation. The transformants are plated on an agar medium to form colonies, and colony hybridization is conducted using the $^{32}P$-labeled probes. The colony of *E. coli* showing homology with the probe is selected and isolated.

(5) The recombinant plasmid DNA is extracted from the selected *E. coli* cells and the restriction enzyme cleavage map is constructed. Subsequently, the region irrelevant to cephalosporin acetylhydrolase gene is eliminated. The base sequence of the *B. subtilis*-derived DNA fragment encoding the cephalosporin acetylhydrolase is determined. Amino acid sequence deduced from the determined DNA base sequence is then compared with the partial amino acid sequence, molecular weight, terminal amino acid analysis and amino acid composition analysis of cephalosporin acetylhydrolase, and the structural gene for the cephalosporin acetylhydrolase is determined.

(6) The DNA fragment containing cephalosporin acetylhydrolase gene is properly modified and then introduced into a gene expression vector for E. coli so that the structural gene is connected after a promoter derived from E. coli, to construct a recombinant plasmid for expression.

(7) The recombinant expression plasmid obtained above is introduced into an E. coli host by transformation to prepare a novel E. coli strain producing cephalosporin acetylhydrolase.

The procedures employed in the above steps are known to those skilled in the art and can be readily carried out according to an experimental protocol disclosed in standard text books, such as "Molecular Cloning", T. Maniatis et al., Cold Spring Harbor Laboratory (1982). All of the materials used, such as enzymes and reagents, are commercially available and may be used according to the supplier's instructions.

E. coli used as a host may be a strain of E. coli K-12 derivatives such as HB101, DH1, C600, JM103, JM105 and JM109. As an E. coli vector used in cloning, a plasmid vector such as pUC13, pBR322 and pAT153 as well as a phage vector such as λgt10 can be exemplified. The abovementioned hosts and vectors are commercially available and easily obtainable.

In the above step (1), the amino acid sequencing of a protein is known (for example, a commercially available automated amino acid sequencer may be used). In the above step (2), the synthesis of the oligonucleotides can be carried out using a commercially available DNA synthesizer according to the supplier's protocol. In the above step (5), the determination of the DNA base sequence can be performed according to the method by Sanger et al., *Proc. Natl. Acad. Sci. U.S.A.*, 74, 5463–5467(1977), where a known M13 vector system is employed.

In the above step (6), the construction of a plasmid to direct efficient expression of the desired gene in E. coli may be carried out by inserting the DNA fragment containing the desired cephalosporin acetylhydrolase structural gene into an expression vector (pKK223-3, pBS, pDR540, pPL-lambda, etc.) containing a suitable promoter (Lac, Tac, Trc, Trp, $P_L$, etc.) functional in a host and Shine-Dalgarno (SD) sequence, or into an ATG vector (pKK233-2, etc.) which additionally contains the translational initiation codon ATG. Introduction of the expression plasmid into a suitable host (for example, such a strain as E. coli JM103, JM109, HB101 and C600) yields a microorganism efficiently expressing cephalosporin acetylhydrolase.

The expressed cephalosporin acetylhydrolase may be purified according to a conventional purification method, for example, by combining centrifugation, column chromatography and the like.

The present invention is further illustrated by the following Example, but not limited thereto.

EXAMPLE 1

1. Separation and purification of cephalosporin acetylhydrolase and determination of partial amino acid sequence (1) Separation and purification of cephalosporin acetylhydrolase A medium (20 L) composed of 2.5% glucose, 0.75% corn steep liquor, 1.0% amino acids mixture, 0.3% $KH_2PO_4$, and 0.8 ppm $MnSO_4.4H_2O$, pH 7.0 was charged into a 30 L volume of jar-fermentor. After sterilization, B. subtilis (FERM BP-2755) which had been precultured in a medium composed of 0.5% glucose, 0.75% corn steep liquor, 0.5% amino acids mixture, and 0.02% $KH_2PO_4$, pH 7.0, was poured into the medium so as to obtain 6% of inoculum size. After 48 hours of cultivation at 28° C., activated charcoal was added to the cultured fluid to 1%, and stirred for 2 hours. Subsequent filtration gave a crude enzyme solution as filtrate. To the crude enzyme solution, DEAE Sephadex A-50 (Pharmacia) was added to 0.7%, and the mixture was adjusted to pH 8.0 using 2N NaOH and then stirred for one hour. After filtration, DEAE Sephadex A-50, on which cephalosporin acetylhydrolase activity was adsorbed, was washed with 50 mM Tris-HCl buffer (pH 8.0)(4 L) containing 0.1M NaCl, and the activity was then eluted with the same buffer containing 0.4M NaCl. After concentration and desalting by an ultrafiltration apparatus (Tosoh), the activity was adsorbed onto a column filled with DEAE Sepharose CL-6B (Pharmacia) which had been previously equilibrated with the same buffer. The column was washed with the same buffer and subsequently that containing 0.15M NaCl, and the activity was then eluted with the same buffer containing 0.2M NaCl. After concentration and desalting by ultrafiltration, purification with high performance liquid chromatography (hereafter referred to as HPLC) was performed. DEAE Toyopearlpak 650M (Tosoh) was used as the column. The activity was eluted by concentration gradient elution method where salt concentration was sequentially raised. Thus, starting with the same buffer containing 0.15M NaCl, the concentration of NaCl was sequentially raised to 0.5M. Fractions containing the eluted activity were collected, concentrated by ultrafiltration, and then purified by HPLC using a molecular sieve column. TSK-G3000 (Tosoh) was used as the column and 0.2M phosphate buffer (pH 7.0) was used as the mobile phase. The eluted active fractions were collected, concentrated by ultrafiltration, and then purified by HPLC using a reversed phase column. Microbondapak $C_{18}$ (Waters) was used as the column and the elution was carried out by concentration gradient elution method where acetonitrile concentration was sequentially raised. Thus, starting with aqueous system containing 0.1% trifluoroacetic acid, the acetonitrile concentration was raised to the final concentration of 98%. The fractions containing the eluted cephalosporin acetylhydrolase were concentrated under reduced pressure at 50° C. and the residue was dissolved in 0.5M Tris-HCl buffer (pH 8.0) containing 6M guanidine hydrochloride. To the solution, EDTA (ethylenediaminetetraacetic acid) was added to obtain 2 mM of concentration, and 200-fold mole amount of 2-mercaptoethanol relative to cephalosporin acetylhydrolase was added to the solution, and the reduction was performed at 37° C. for 4 hours under the nitrogen atmosphere. Subsequently, 190-fold mole amount of sodium iodoacetate relative to cephalosporin acetylhydrolase was added to the solution and reacted at 37° C. for 10 minutes in the dark to perform reductive carboxymethylation. Then, the purification by HPLC using a reversed phase column was conducted again according to the above method. The resulting cephalosporin acetylhydrolase fractions were analyzed by SDS-polyacrylamide gel electrophoresis (SDS-PAGE) according to the procedure of Laemmli, Nature, 227, 680–685(1970). Only a single band was detected at a position of molecular weight of 35 kD, implying that purification was achieved homogeneously. In addition, the facts that the purified cephalosporin acetylhydrolase solubilized in 0.1M Tris-HCl buffer (pH 8.0) containing 7M urea was reactivated by 10-fold dilution with 0.1M phosphate buffer (pH 7.0), and that the activity was eluted at a position of molecular weight of 280 kD by a molecular sieve column chromatography using the above-mentioned HPLC suggested that the cephalosporin acetylhydrolase in a natural form is the octamer consisting of homogeneous subunits.

On the other hand, the molecular weight determined using the procedure of Hedrick et al., Arch. Biochem. Biophys., 126, 155–164(1968) was about 150 kD and the activity was detected at the relevant position, which suggested that the tetramer is also active.

Amino acid terminal analysis of the purified cephalosporin acetylhydrolase by Edman degradation and hydrazine hydrolysis identified the amino terminus to be methionine and the carboxy terminus to be glycine.

(2) Determination of partial amino acid sequence of cephalosporin acetylhydrolase The purified cephalosporin acetylhydrolase (1 mg) was solubilized in 0.1M Tris-HCl buffer (pH 8.8)(1.0 ml) containing 2M urea, and lysylendopeptidase (0.01 mg) was added to the solution and the mixture was reacted at 37° C. for 4 hours. The reaction mixture was then separated by HPLC. Microbondapak $C_{18}$ (Waters) was used as the column and the elution was carried out by concentration gradient elution method sequentially raising acetonitrile concentration. Thus, starting with aqueous system containing 0.1% trifluoroacetic acid, the acetonitrile concentration was raised to final concentration of 98%. The detection was carried out at 214 nm. Of the separated peaks, distinctive fractions having a long retention time were collected and again purified using the same reversed phase column, and the amino acid sequence of the peptide was analyzed using a gas phase automated amino acid sequencer (Applied Biosystems) to determine the amino acid sequence from amino terminus to 34th amino acid of the peptide fragment, as shown in FIG. 3.

2. Synthesis of DNA probes and labeling the 5'-termini

The sequence (SEQ. ID. No. 4) underlined in the amino acid sequence in FIG. 3 obtained by the above step 1 was selected and a pool of oligonucleotides corresponding to all of the genetically possible DNA base sequences (SEQ. ID. NOS. 5 and 6) deduced from this amino acid sequence were synthesized. As shown in FIG. 4, 4 groups of the oligonucleotides, which were designated as DNA probes CAH-RM1 (SEQ. ID. NO. 7), CAH-RM2 (SEQ. ID. NO. 8) CAH-RM3 (SEQ. ID. NO. 9) and CAH-RM4 (SEQ. ID. NO. 10), were synthesized. Synthesis of the oligonucleotides was conducted using automated DNA synthesizer ZEON-GENET A-II (Nihon Zeon).

5'-Termini of the resulting DNA probes were labeled using T4 polynucleotide kinase and [$\gamma$-$^{32}$P]ATP according to the procedure of Wallace et al., Nucleic Acids Res., 6, 3543–3557(1979).

3. Extraction and purification of chromosomal DNA from B. subtilis and Southern hybridization Cells of B. subtilis (FERM BP-2755) were treated with lysozyme followed by sodium N-lauroylsarcosinate, and the chromosomal DNA was extracted and purified from the resulting lysate by CsCl-ethidium bromide equilibrium density gradient ultracentrifugation according to the procedure of Harris-Warrick et al., Proc. Natl. Acad. Sci. U.S.A., 72, 2207–2211(1975). The DNA (1 μg) was digested with various restriction enzymes (each about 10 units) under a suitable condition, and the reactants were electrophoresed on 0.8% agarose gel. After the analysis of restriction enzyme cleavage pattern, the gel was subjected to Southern hybridization according to the procedure of Southern et al., J. Mol. Biol., 98, 503–517(1975). The gel was treated with 1.5M NaCl solution containing 0.5N NaOH at room temperature for 1 hour to denature DNA, and then neutralized in 1M Tris-HCl buffer (pH 7.0) containing 1.5M NaCl at room temperature for 1 hour. A nitrocellulose membrane was then placed on the gel to transfer the DNA from the gel to the membrane. Using the DNA-transferred nitrocellulose membrane, the hybridization with the labeled probes was carried out. The hybridization was conducted at 38° C. overnight using 4-fold concentration of SSC (1×SSC: 0.15M NaCl, 0.015M sodium citrate, pH 7.0), 10-fold concentration of Denhardt's solution (1×Denhardt's solution: 0.02% Ficoll, 0.02% polyvinylpyrrolidone, 0.02% bovine serum albumin), and about $1 \times 10^6$ cpm/ml of the labelled probes. The membrane was washed several times with 4-fold concentration of SSC at room temperature, and then subjected to autoradiography. In addition, the washing temperature of the membrane was raised stepwise, and the membrane was provided for autoradiography repeatedly in each case. It was found that several DNA bands show positive signals even at the high washing temperatures such as 48° C. and 53° C., and that the sizes of the hybridizing bands differ each other depending on the restriction enzymes employed. Out of the DNA fragments showing positive signals 2.5–3 kb DraI digested and 4–4.5 kb HindIII digested fragments were preferable for gene cloning because their sizes were larger than the desired gene.

4. Cloning of cephalosporin acetylhydrolase gene (1) Construction of gene library To the chromosomal DNA (12 μg) from B. subtilis extracted and purified in the above step 3, restriction enzyme DraI (about 120 units) was added and incubated at 37° C. for 90 minutes. The reactant was then extracted with equal volume of phenol, and ethanol was added to the resulting aqueous layer to precipitate DNA. The resulting DNA was dissolved in TE buffer [10 mM Tris-HCl, 1 mM EDTA, pH 8.0](60 μl), the resultant solution was electrophoresed on 0.8% agarose gel, and a region of the gel corresponding to a size of 2–4 kb was excised. DNA fragments were eluted and recovered from the gel using a commercially available kit (Bio 101, GENECLEAN), and dissolved in TE buffer (30 μl).

On the other hand, pUC13 was used as a vector for constructing a gene library. pUC13 (10 μg) was mixed with restriction enzyme SmaI (about 100 units), incubated at 37° C. for 140 minutes, and then treated at 65° C. for 10 minutes. Alkaline phosphatase (BAP)(about 20 units) was added to the mixture and further reacted at 65° C. for 80 minutes. Phenol extraction followed by ethanol precipitation of DNA was carried out according to the above procedure and the DNA was finally dissolved in TE buffer (50 μl).

The solution containing the DraI digested fragments of B. subtilis chromosome (7.5 μl) and the solution containing the SmaI-BAP treated fragments of vector pUC13 (2.5 μl) were combined, and the mixture was incubated with T4 DNA ligase at 6° C. for 20 hours to ligate the fragments, forming a recombinant DNA. The resultant recombinant DNA was used to transform E. coli HB101 strain according to the procedure of Hanahan et al., J. Mol. BioS., .166, 557-580(1983). Subsequently, colonies were allowed to form on a nitrocellulose membrane placed on L-broth [1% bacto-tryptone, 0.5% yeast extract, 0.5% NaCl (pH 7.3)]agar medium containing 40 μg/ml ampicillin. These colonies were designated as the gene library of B. subtilis.

(2) Selection of cephalosporin acetylhydrolasepositive clone by colony hybridization The colonies formed on the nitrocellulose membrane in the above step (1) were replicated on another nitrocellulose membrane. The replica membrane was placed on L-broth agar medium containing 40 μg/ml ampicillin and incubated at 37° C. for 3 hours. Then, the membrane was transferred on L-broth agar medium containing 250 μg/ml chloramphenicol and incubated at 37° C. overnight. Colony hybridization was then carried out substantially according to the procedure of Grunstein et al., Proc. Natl. Acad. Sci. U.S.A., 72, 3961-3965(1975). Thus, the membrane was treated with 0.5N NaOH (for 10-15 minutes) to effect lysis of colonies and denaturation of DNA. Subsequently, the membrane was neutralized with 1M Tris-HCl buffer (pH 7.2) for 5-10 minutes and further treated with 1M Tris-HCl buffer (pH 8.0) containing 1.5M NaCl for 10-15 minutes. After the membrane was baked under reduced pressure at 80° C. for 2 hours to immobilize DNA to the membrane, the immobilized DNA was hybridized with the labeled probe CAH-RM2. The reaction was carried out in a solution containing 4-fold concentration of SSC, 10-fold concentration of Denhardt's solution and about $2 \times 10^6$ cpm/ml of the labelled probe at 38° C. for 16 hours. Subsequently, the membrane was washed 3-4 times with 4-fold concentration of SSC at room temperature, then washed at 38° C. for 2 minutes, and subjected to autoradiography (exposure condition: —80° C., 3 hours). In order to examine the correlation between washing temperature and intensity of signal on the autoradiography, the washing temperature was further raised stepwise and the autoradiography was conducted in each case. The washing was carried out at 43° C., 48° C. and 53° C. each for 2 minutes.

As a result, it was found that 3 of about 30,000 colonies showed positive signals even at the high washing temperature. These colonies were liquid-cultured in L-broth (5ml) containing 40 μg/ml ampicillin at 37° C. overnight and recombinant plasmids were prepared [procedure of Birnboim et al., Nucleic Acids Res., 7, 1513-1523(1979)]. These plasmids were cleaved and fragmented with a restriction enzyme such as EcoRI, HindIII and PvuII for which the vector DNA (pUC13) has a cleavage site. Then, electrophoresis was carried out on agarose gel and Southern hybridization with the labeled probe was carried out. As a result, it was found that two of three recombinant plasmids contained a restriction enzyme digested fragment clearly hybridizing with the DNA probe. The size of the hybridizing fragments differed between the two positive plasmids, and therefore, the DNA fragments inserted into the vector DNA appeared different each other. Accordingly, respective recombinant plasmids were distinguished and designated as pCAH01 and pCAH02.

5. Identification of positive clone and determination of base sequence (1) Identification of positive clone In the course of attempts to prepare restriction enzyme cleavage maps for the recombinant plasmids pCAH01 and pCAH02 by cleaving them with various restriction enzymes, it was found that plasmid pCAH01 has two different DraI digested fragments and plasmid pCAH02 has at least three different DraI digested fragments inserted into the SmaI site on the vector DNA, and that the DNA probe hybridizes with one of these DraI fragments. Consequently, the recombinant plasmid pCAH01 was used in the subsequent procedures. The restriction enzyme cleavage map of plasmid pCAH01 was depicted in FIG. 5 together with the position at where the DNA probe hybridized.

Since plasmid pCAH01 contains two exogenous DraI fragments derived from the chromosomal DNA of B. subtilis (1.8 kb and 2.5 kb) and only the 2.5 kb fragment hybridizes with the DNA probe, the 1.8 kb DraI fragment was deleted from the plasmid. DraI-PstI fragment (2.6 kb) containing the 2.5 kb fragment was removed from plasmid pCAH01 and inserted into SmaI-PstI site of vector plasmid pUC13 to obtain a miniaturized recombinant plasmid pCAH03 (5.3 kb). The restriction enzyme cleavage map of the recombinant plasmid pCAH03 was shown in FIG. 6.

(2) Determination of base sequence

From the recombinant plasmid pCAH03, 0.24 kb EcoRI-HindIII fragment to which the DNA probe had hybridized was removed and its DNA base sequence was determined according to the procedure of Sanger et al., Proc. Natl. Acad. Sci. U.S.A., 74, 5463-5467(1977). As a result, a base sequence corresponding to the partial amino acid sequence cephalosporin acetylhydrolase obtained in the above step 1 was found in the EcoRI-HindIII fragment, revealing that the fragment contains a part of cephalosporin acetylhydrolase gene. By subsequent determination of the base sequence between DraI and HindIII sites (0.38 kb) as well as between ECORI and EcoRI sites (1.45 kb) on the basis of the restriction enzyme cleavage map of plasmid pCAH03, the base sequence of about 2 kb between DraI and EcoRI sites was revealed as shown in FIG. 7. This proved the presence of a base sequence encoding a protein composed of 318 amino acid residues containing methionine encoded by translational initiation codon ATG. In addition, the putative protein encoded by the above base sequence showed a good coincidence with the cephalosporin acetylhydrolase with respect to their molecular weight, amino-terminal and carboxy-terminal amino acids, as well as amino acid composition of lysylendopeptidase digested fragments and therefore, it was believed that this protein must be cephalosporin acetylhydrolase Thus, it was proved that the structural gene of cephalosporin acetylhydrolase was entirely contained in the B. subtilis-derived DNA fragment on plasmid pCAH03.

6. Construction of expression plasmid

The cloned *B. subtilis*-derived DNA fragment on plasmid pCAH03 contains a region other than the cephalosporin acetylhydrolase gene, and therefore, the region considered to be irrelevant to phenotypic expression of the gene was deleted according to the process depicted in FIG. 8.

In order to drive high expression of a heterologous gene in *E. coli*, it is generally effective to construct an expression plasmid in which a desired structural gene is connected immediately after a sequence consisting of a promoter having a high expression efficiency, SD sequence and translational initiation codon ATG. Thus, in order to produce a large amount of cephalosporin acetylhydrolase in *E. coli*, an expression plasmid was constructed using a vector containing a promoter, SD sequence and ATG, according to the process depicted in FIG. 9. In the process of the construction, the cephalosporin acetylhydrolase structural gene can be prepared as follows. A region entirely containing the desired gene is cloned into a vector of M13 mp series to obtain a single-stranded DNA. According to a so-called primer extension method, using as a primer an oligonucleotide specifying several amino acids excluding methionine on the amino terminal sequence of cephalosporin acetylhydrolase, a DNA fragment in which only the cephalosporin acetylhydrolase structural gene moiety is double-stranded is obtained.

Figure 10:
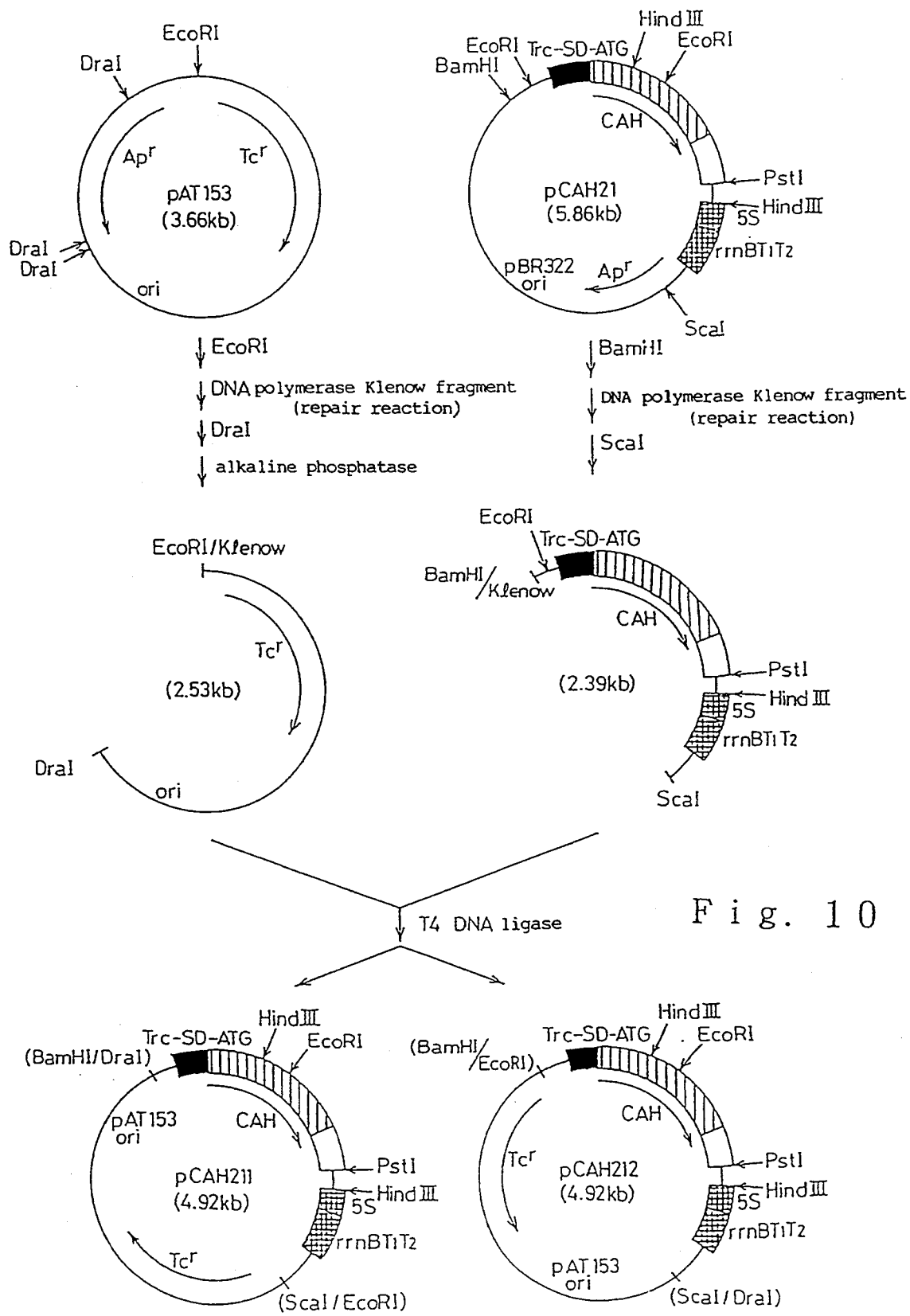
FIG. 10 depicts the construction of expression plasmids pCAH211 and pCAH212 used in *E. coli.*

FIG. 10 shows the process for constructing a modified expression plasmid which shows increased copy number as compared with the expression plasmid prepared by the process in FIG. 9, and which bears tetracycline (Tc$^r$) resistance marker instead of ampicillin (Ap$^r$) resistance A marker.

The followings are the more detailed description of each step.

(1) Construction of miniaturized plasmid

In order to shorten a downstream region of the cephalosporin acetylhydrolase structural gene (abbreviated as CAH in FIG. 8), plasmid pCAH03 was cleaved with EcoRV and BanHI, about 4.1 kb DNA fragment obtained was purified, and then the 3' recessed termini created by BamHI digestion were filled using DNA polymerase Klenow fragment (FIG. 8). After further purification, ligation was carried out using T4 DNA ligase to construct miniaturized plasmid pCAH10 containing the cephalosporin acetylhydrolase gene.

(2) Preparation of single-stranded DNA for constructing expression plasmid

The miniaturized plasmid pCAH10 prepared in the above step (1) was cleaved with SacI and SalI and about 1.5 kb fragment obtained was purified and recovered as a SacI-SalI fragment. On the other hand, double-stranded phage M13 mpII DNA was cleaved with SacI and SalI. Then, to the latter was added the above SacI-SalI fragment and ligated with T4 DNA ligase to construct double-stranded phage M13-CAH DNA which contained the complete cephalosporin acetylhydrolase gene. Subsequently, its single-stranded DNA was prepared according to the procedure of Messing, *Methods in Enzymology*, 101, 20–78(1983).

(3) Primer extension

A region containing cephalosporin acetylhydrolase structural gene was prepared by eliminating a protein-noncoding region derived from *B. subtilis*, which locates upstream the initiation site (ATG) of cephalosporin acetylhydrolase, in substantial accordance with the procedure of Goeddel et al., *Nucleic Acids Res.*, 8, 4057–4074(1980). An oligonucleotide having a base sequence corresponding to the 2nd amino acid glutamine to the 7th amino acid proline from amino terminus of cephalosporin acetylhydrolase was synthesized as a primer to be used in primer extension and designated as CAH-P1. The primer CAH-P1 (3 pmole) was then added to the single-stranded DNA (7.5 μg) of phage M13-CAH prepared in the above step (2), and the mixture was heated to 60° C. for 20 minutes and then allowed to stand to room temperature. Subsequently, to the mixture were added dATP, dCTP, dGTP and dTTP (each 0.25 mM) as well as DNA polymerase Klenow fragment (2 units), and the primer extension was carried out at 37° C. for 2 hours in a reaction mix (20 μl) of 7 mM Tris-HCl buffer (pH 7.5), 7 mM MgCl$_2$, 0.1 mM EDTA, and 20 mM NaCl. After the reaction, phenol extraction and ethanol precipitation were conducted. The DNA was dissolved in a small amount of distilled water, to which S1 nuclease (4 units) was added and incubated at 37° C. for 30 minutes in a reaction mix (40 μl) of 30 mM sodium acetate (pH 4.6), 100 mM NaCl and 1 mM ZnSO$_4$ to digest remaining single-stranded DNA. The solution containing the double-stranded DNA fragment obtained was subjected to phenol extraction followed by ethanol precipitation, and the DNA was treated with DNA polymerase Klenow fragment according to the above procedure for repair reaction of the termini.

(4) Construction of expression plasmid

The vector pKK233-2 (ampicillin resistance) used in the present example for constructing an expression plasmid is commercially available from Pharmacia. The vector is a member of ATG vectors, which contains Trc promoter and can be cleaved immediately after initiation codon ATG by digestion with restriction enzyme NcoI and filling of the 3' recessed termini. As depicted in FIG. 9, the DNA fragment obtained in the above step (3), which contains the cephalosporin acetylhydrolase structural gene, was cleaved with PstI, and 1.27 kb DNA fragment was separated and purified. On the other hand, pKK233-2 containing Trc promoter was cleaved with NcoI and treated with DNA polymerase Klenow fragment. The resulting fragment was then cleaved with PstI to obtain about 4.6 kb DNA fragment. Subsequently, the above two fragments were mixed and ligated each other with T4 DNA ligase, the resultant mixture was used to transform *E. coli* JM103 strain, and colonies formed on L-broth agar medium containing 40 μg/ml ampicillin were selected. These colonies were liquid-cultured in L-broth overnight, cells were collected, plasmid DNA was extracted from the cells, and the base sequence near the junction of the ATG vector and the fragment containing cephalosporin acetylhydrolase gene was determined. As a result, an expression plasmid, in which the structural gene of cephalosporin acetylhydrolase excluding amino-terminal methionine had been inserted immediately after the ATG codon, was obtained and designated as pCAH21. Also, *E. coli* harboring the expression plasmid was designated as *E. coli* JM103/pCAH 21.

The replication system of the expression plasmid pCAH21 is derived from pBR322. Accordingly, in order to enhance the copy number of this plasmid to raise the expression level in *E. coli*, its replication region (ori) was changed to that derived from pAT153. Simultaneously, its drug resistance marker was changed from ampicillin resistance (Ap$^r$) to tetracycline resistance (Tc$^r$). A process for modifying the plasmid was depicted in FIG. 10. Plasmid pCAH21 was first cleaved with BamHI and treated with DNA polymerase Klenow fragment. Then, the resulting fragment was cleaved with ScaI to obtain about 2.4 kb DNA fragment containing Trc promoter, cephalosporin acetylhydrolase gene and $T_1T_2$ terminator of 5S ribosomal RNA (5SrrnBT$_1$T$_2$). Commercially available plasmid pAT153 was used as the vector plasmid. Plasmid pAT153 was cleaved with EcoRI, treated with DNA polymerase Klenow fragment, and then cleaved with DraI. Furthermore, in order to prevent selfligation of the vector, alkaline phosphatase treatment was conducted, and about 2.5 kb DNA fragment containing the replication region and tetracycline resistance gene from pAT153 was prepared. Then, the above two DNA fragments were mixed and ligated with T4 DNA ligase, the resultant mixture was used to transform E. coli JM103 strain, and colonies formed on L-broth agar medium containing 20 µg/ml tetracycline were selected. After these colonies were cultured in L-broth overnight, cells were collected, and the plasmid DNA was extracted from the cells and analyzed by restriction enzyme cleavage. As a result, two recombinant plasmids which differ in orientation of ligation were obtained. One plasmid in which the orientation of cephalosporin acetylhydrolase gene was identical with that of tetracycline resistance gene was designated as pCAH211 and another plasmid in which these genes were reversely inserted was designated as pCAH212. Also, E. coli strains harboring these recombinant expression plasmids were designated as E. coli JM103/pCAH211 and E. coli JM103/pCAH212, respectively.

7. Expression of cephalosporin acetylhydrolase gene in E. coli (1) Expression of cephalosporin acetylhydrolase gene E. coli JM103/pCAH211 or E. coli JM103/pCAH212 was inoculated on 2-fold concentration of L-broth (50 ml) containing 20 µg/ml tetracycline (in 0.5 L volume flask) and cultured at 37° C. for 24 hours with shaking. An aliquot (0.5 ml) of the cultured fluid was centrifuged to collect cells. The cells were suspended in 0.1M phosphate buffer (pH 7.0)(0.5ml) and disrupted with ultrasonicator. The supernatant obtained by centrifuging the solution was used as a sample solution containing the desired enzyme. On the other hand, the supernatant obtained by centrifuging the cultured fluid of B. subtilis (FERM BP-2755) obtained in the above step 1 was used as an enzyme solution for comparison. Cephalosporin acetylhydrolase acts not only on cephalosporin C and 7-ACA but also on p-nitrophenyl acetate (hereafter abbreviated to pNPA) to form colored substance, p-nitrophenol (hereafter abbreviated to pNP). The pNP is detectable spectrophotometrically, and therefore, the procedure in which pNPA is used as a substrate was adopted as a simple determination method for cephalosporin acetylhydrolase activity. Reaction was carried out in a mixture (3ml) containing 0.02% pNPA, 0.1M phosphate buffer (pH 6.8) and the above-mentioned enzyme solution at 30° C., and the enzyme activity was determined by measuring absorbance at 400nm using a spectrophotometer. The amount of the enzyme producing 1 µmole of pNP per minute under the condition of pH 6.8 and 30° C. of temperature was defined as one unit(U). As a result, it was found that the enzyme activities per cultured fluid of E. coli JM103/pCAH211 and E. coli JM103/pCAH212 were 9.9U/ml and 12.4U/ml, respectively. On the other hand, the enzyme activity of B. subtilis was 0.36 U/ml.

Furthermore, a plasmid was constructed in which Trc promoter and SD-ATG sequence of expression plasmid pCAH211 were replaced by Trp promoter and SD-ATG sequence derived from E. coli tryptophan operon. After the plasmid was introduced into E. coli JM109 by transformation, the resulting transformant was cultured in a similar manner as described above, and 75.5 U/ml of enzyme activity per cultured fluid was obtained.

The amount of cephalosporin acetylhydrolase produced can be increased by growing E. coli harboring these expression plasmids in a suitable medium under a suitable culture condition using a large scale culture apparatus such as jar-fermentor.

(2) Deacetylation of cephalosporin C and 7-ACA

Deacetylation by an enzyme solution from E. coli JM103/pCAH212 was carried out using cephalosporin C or 7-ACA as a substrate. The reaction was conducted at 37° C. for 40 minutes after adding the enzyme solution (0.2ml) to 0.1M phosphate buffer (pH 7.0)(1.0ml) containing 10 mM of the substrate, and terminated by addition of 0.2M acetate buffer (pH 4.0)(1.2ml). The resulting solution was subjected to HPLC, and deacetylcephalosporin C or deacetyl-7-ACA was measured. Cosmosil 5C$_8$ (Nacalai tesque) was used as a column and the elution was carried out by concentration gradient elution method where methanol concentration was sequentially raised. Thus, using a solution containing 20 mM NaH$_2$PO$_4$, and 5 mM tetra-n-butylammonium hydroxide (TBAH), the methanol concentration was raised to 20%. Detection of the deacetylated products was carried out at 254nm. Activity of cephalosporin acetylhydrolase was defined as follows. Thus, the amount of the enzyme producing 1 µmole of the product per minute under the condition of pH 7.0 and 37° C. of temperature is defined as one unit(U). As a result, it was found that the activity per cultured fluid of the enzyme solution of [E. coli JM103/pCAH212 was 7.4 U/ml for both cephalosporin C and 7-ACA.

(3) Structure of recombinant cephalosporin acetylhydrolase

Determination of molecular weights of the active form and subunit of cephalosporin acetylhydrolase produced in E. coli gave the same results as obtained in the above step 1, suggesting that the recombinant cephalosporin acetylhydrolase also exists in an octamer form similar to the natural form.

Furthermore, the recombinant cephalosporin acetylhydrolase was purified by HPLC using a reversed phase column. Terminal analysis by Echnan degradation and hydrazine hydrolysis revealed that the amino and carboxy termini of the enzyme were methionine and glycine, respectively, and identical with those of natural form. In addition, determination of the amino terminal sequence using an automated amino acid sequencer revealed that the amino acid sequence to 25th amino acid was entirely identical with that deduced from the structural gene (FIG. 2).

Effects of the Invention

As described in the above Example in detail, the present inventors have confirmed that a great efficient production of cephalosporin acetylhydrolase is possible by cloning a gene encoding cephalosporin acetylhydrolase produced by B. subtilis and constructing a recombinant plasmid containing the gene by the use of a vector expressible in *E. coli*. This provides a premise for extensive application of this enzyme. In addition, the DNA fragment containing the cloned cephalosporin acetylhydrolase gene provides an extremely powerful means of advantageously utilizing the function of cephalosporin acetylhydrolase.

---

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 317 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Gln Leu Phe Asp Leu Pro Leu Asp Gln Leu Gln Thr Tyr Lys Pro Glu
  1               5                  10                  15
Lys Thr Ala Pro Lys Asp Phe Ser Glu Phe Trp Lys Leu Ser Leu Glu
             20                  25                  30
Glu Leu Ala Lys Val Gln Ala Glu Pro Asp Leu Gln Pro Val Asp Tyr
         35                  40                  45
Pro Ala Asp Gly Val Lys Val Tyr Arg Leu Thr Tyr Lys Ser Phe Gly
     50                  55                  60
Asn Ala Arg Ile Thr Gly Trp Tyr Ala Val Pro Asp Lys Gln Gly Pro
 65                  70                  75                  80
His Pro Ala Ile Val Lys Tyr His Gly Tyr Asn Ala Ser Tyr Asp Gly
                 85                  90                  95
Glu Ile His Glu Met Val Asn Trp Ala Leu His Gly Tyr Ala Ala Phe
                100                 105                 110
Gly Met Leu Val Arg Gly Gln Gln Ser Ser Glu Asp Thr Ser Ile Ser
            115                 120                 125
Leu His Gly His Ala Leu Gly Trp Met Thr Lys Gly Ile Leu Asp Lys
130                 135                 140
Asp Thr Tyr Tyr Tyr Arg Gly Val Tyr Leu Asp Ala Val Arg Ala Leu
145                 150                 155                 160
Glu Val Ile Ser Ser Phe Asp Glu Val Asp Glu Thr Arg Ile Gly Val
                165                 170                 175
Thr Gly Gly Ser Gln Gly Gly Gly Leu Thr Ile Ala Ala Ala Ala Leu
            180                 185                 190
Ser Asp Ile Pro Lys Ala Ala Val Ala Asp Tyr Pro Tyr Leu Ser Asn
        195                 200                 205
Phe Glu Arg Ala Ile Asp Val Ala Leu Glu Gln Pro Tyr Leu Glu Ile
    210                 215                 220
Asn Ser Phe Phe Arg Arg Asn Gly Ser Pro Glu Thr Glu Val Gln Ala
225                 230                 235                 240
Met Lys Thr Leu Ser Tyr Phe Asp Ile Met Asn Leu Ala Asp Arg Val
                245                 250                 255
Lys Val Pro Val Leu Met Ser Ile Gly Leu Ile Asp Lys Val Thr Pro
            260                 265                 270
Pro Ser Thr Val Phe Ala Ala Tyr Asn His Leu Glu Thr Glu Lys Glu
        275                 280                 285
Leu Lys Val Tyr Arg Tyr Phe Gly His Glu Tyr Ile Pro Ala Phe Gln
    290                 295                 300
Thr Glu Lys Leu Ala Phe Phe Lys Gln His Leu Lys Gly
305                 310                 315
```

(2) INFORMATION FOR SEQ ID NO:2:

(i) SEQUENCE CHARACTERISTICS:
        (A) LENGTH: 957 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:2:

```
ATG CAA CTA TTC GAT CTG CCG CTC GAC CAA TTG CAA ACA TAT AAG CCT       48
Met Gln Leu Phe Asp Leu Pro Leu Asp Gln Leu Gln Thr Tyr Lys Pro
 1               5                  10                  15

GAA AAA ACA GCA CCG AAA GAT TTT TCT GAG TTT TGG AAA TTG TCT TTG       96
Glu Lys Thr Ala Pro Lys Asp Phe Ser Glu Phe Trp Lys Leu Ser Leu
                 20                  25                  30

GAG GAA CTT GCA AAA GTC CAA GCA GAA CCT GAT CTA CAG CCG GTT GAC      144
Glu Glu Leu Ala Lys Val Gln Ala Glu Pro Asp Leu Gln Pro Val Asp
             35                  40                  45

TAT CCT GCT GAC GGA GTA AAA GTG TAC CGT CTC ACA TAT AAA AGC TTC      192
Tyr Pro Ala Asp Gly Val Lys Val Tyr Arg Leu Thr Tyr Lys Ser Phe
         50                  55                  60

GGA AAC GCC CGC ATT ACC GGA TGG TAC GCG GTG CCT GAC AAG CAA GGC      240
Gly Asn Ala Arg Ile Thr Gly Trp Tyr Ala Val Pro Asp Lys Gln Gly
 65                  70                  75                  80

CCG CAT CCG GCG ATC GTG AAA TAT CAT GGC TAC AAT GCA AGC TAT GAT      288
Pro His Pro Ala Ile Val Lys Tyr His Gly Tyr Asn Ala Ser Tyr Asp
                 85                  90                  95

GGT GAG ATT CAT GAA ATG GTA AAC TGG GCA CTC CAT GGC TAC GCC GCA      336
Gly Glu Ile His Glu Met Val Asn Trp Ala Leu His Gly Tyr Ala Ala
            100                 105                 110

TTC GGC ATG CTT GTC CGC GGC CAG CAG AGC AGC GAG GAT ACG AGT ATT      384
Phe Gly Met Leu Val Arg Gly Gln Gln Ser Ser Glu Asp Thr Ser Ile
            115                 120                 125

TCA CTG CAC GGT CAT GCT TTG GGC TGG ATG ACG AAA GGA ATT CTT GAT      432
Ser Leu His Gly His Ala Leu Gly Trp Met Thr Lys Gly Ile Leu Asp
        130                 135                 140

AAA GAT ACA TAC TAT TAC CGC GGT GTT TAT TTG GAC GCC GTC CGC GCG      480
Lys Asp Thr Tyr Tyr Tyr Arg Gly Val Tyr Leu Asp Ala Val Arg Ala
145                 150                 155                 160

CTT GAG GTC ATC AGC AGC TTC GAC GAG GTT GAC GAA ACA AGG ATC GGT      528
Leu Glu Val Ile Ser Ser Phe Asp Glu Val Asp Glu Thr Arg Ile Gly
                165                 170                 175

GTG ACA GGA GGA AGC CAA GGC GGA GGT TTA ACC ATT GCC GCA GCA GCG      576
Val Thr Gly Gly Ser Gln Gly Gly Gly Leu Thr Ile Ala Ala Ala Ala
            180                 185                 190

CTG TCA GAC ATT CCA AAA GCC GCG GTT GCC GAT TAT CCT TAT TTA AGC      624
Leu Ser Asp Ile Pro Lys Ala Ala Val Ala Asp Tyr Pro Tyr Leu Ser
            195                 200                 205

AAC TTC GAA CGG GCC ATT GAT GTG GCG CTT GAA CAG CCG TAC CTT GAA      672
Asn Phe Glu Arg Ala Ile Asp Val Ala Leu Glu Gln Pro Tyr Leu Glu
        210                 215                 220

ATC AAT TCC TTC TTC AGA AGA AAT GGC AGC CCG GAA ACA GAA GTG CAG      720
Ile Asn Ser Phe Phe Arg Arg Asn Gly Ser Pro Glu Thr Glu Val Gln
225                 230                 235                 240

GCG ATG AAG ACA CTT TCA TAT TTC GAT ATT ATG AAT CTC GCT GAC CGA      768
Ala Met Lys Thr Leu Ser Tyr Phe Asp Ile Met Asn Leu Ala Asp Arg
                245                 250                 255

GTG AAG GTG CCT GTC CTG ATG TCA ATC GGC CTG ATT GAC AAG GTC ACG      816
Val Lys Val Pro Val Leu Met Ser Ile Gly Leu Ile Asp Lys Val Thr
            260                 265                 270

CCG CCG TCC ACC GTG TTT GCC GCC TAC AAT CAT TTG GAA ACA GAG AAA      864
```

| | | | | | | | | | | | | | | |
|---|---|---|---|---|---|---|---|---|---|---|---|---|---|---|
| Pro | Pro | Ser | Thr | Val | Phe | Ala | Ala | Tyr | Asn | His | Leu | Glu | Thr | Lys |
| | | 275 | | | | | 280 | | | | 285 | | | |

| | | | | | | | | | | | | | | | |
|---|---|---|---|---|---|---|---|---|---|---|---|---|---|---|---|
| GAG | CTG | AAG | GTG | TAC | CGC | TAC | TTC | GGA | CAT | GAG | TAT | ATC | CCT | GCT | TTT | 912
| Glu | Leu | Lys | Val | Tyr | Arg | Tyr | Phe | Gly | His | Glu | Tyr | Ile | Pro | Ala | Phe |
| | | 290 | | | | 295 | | | | | 300 | | | | |

| | | | | | | | | | | | | | |
|---|---|---|---|---|---|---|---|---|---|---|---|---|---|
| CAA | ACG | GAA | AAA | CTT | GCT | TTC | TTT | AAG | CAG | CAT | CTT | AAA | GGC | TGA | 957
| Gln | Thr | Glu | Lys | Leu | Ala | Phe | Phe | Lys | Gln | His | Leu | Lys | Gly |
| 305 | | | | | 310 | | | | | 315 | | | |

(2) INFORMATION FOR SEQ ID NO:3:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:3:

| | | | | | | | | | | | | | | |
|---|---|---|---|---|---|---|---|---|---|---|---|---|---|---|
| Tyr | His | Gly | Tyr | Asn | Ala | Ser | Tyr | Asp | Gly | Glu | Ile | His | Glu | Met | Val |
| 1 | | | | 5 | | | | | 10 | | | | | 15 |

| | | | | | | | | | | | | | | |
|---|---|---|---|---|---|---|---|---|---|---|---|---|---|---|
| Asn | Trp | Ala | Leu | His | Gly | Tyr | Ala | Ala | Phe | Gly | Met | Leu | Val | Xaa | Gly |
| | | | 20 | | | | | 25 | | | | 30 | | |

Gln Gln (2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:4:

| | | | | | |
|---|---|---|---|---|---|
| Glu | Met | Val | Asn | Trp | Ala |
| 1 | | | | 5 | |

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:5:

GARATGGTNA AYTGGGC    17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:6:

GCCCARTTNA CCATYTC    17

(2) INFORMATION FOR SEQ ID NO:7:

(i) SEQUENCE CHARACTERISTICS:
        (A) LENGTH: 17 base pairs
        (B) TYPE: nucleic acid (C) STRANDEDNESS: single
(D) TOPOLOGY: linear ( i i ) MOLECULE TYPE: other nucleic acid
(A) DESCRIPTION: synthetic oligonucleotide probe ( x i ) SEQUENCE DESCRIPTION: SEQ ID NO:7:

GCCCARTTAA CCATYTC 17

( 2 ) INFORMATION FOR SEQ ID NO:8:

( i ) SEQUENCE CHARACTERISTICS:
(A) LENGTH: 17 base pairs
(B) TYPE: nucleic acid
(C) STRANDEDNESS: single
(D) TOPOLOGY: linear ( i i ) MOLECULE TYPE: other nucleic acid
(A) DESCRIPTION: synthetic oligonucleotide probe ( x i ) SEQUENCE DESCRIPTION: SEQ ID NO:8:

GCCCARTTTA CCATYTC 17

( 2 ) INFORMATION FOR SEQ ID NO:9:

( i ) SEQUENCE CHARACTERISTICS:
(A) LENGTH: 17 base pairs
(B) TYPE: nucleic acid
(C) STRANDEDNESS: single
(D) TOPOLOGY: linear ( i i ) MOLECULE TYPE: other nucleic acid
(A) DESCRIPTION: synthetic oligonucleotide probe ( x i ) SEQUENCE DESCRIPTION: SEQ ID NO:9:

GCCCARTTGA CCATYTC 17

( 2 ) INFORMATION FOR SEQ ID NO:10:

( i ) SEQUENCE CHARACTERISTICS:
(A) LENGTH: 17 base pairs
(B) TYPE: nucleic acid
(C) STRANDEDNESS: single
(D) TOPOLOGY: linear ( i i ) MOLECULE TYPE: other nucleic acid
(A) DESCRIPTION: synthetic oligonucleotide probe ( x i ) SEQUENCE DESCRIPTION: SEQ ID NO:10:

GCCCARTTCA CCATYTC 17

( 2 ) INFORMATION FOR SEQ ID NO:11:

( i ) SEQUENCE CHARACTERISTICS:
(A) LENGTH: 2046 base pairs
(B) TYPE: nucleic acid
(C) STRANDEDNESS: double
(D) TOPOLOGY: linear ( i i ) MOLECULE TYPE: genomic DNA ( x i ) SEQUENCE DESCRIPTION: SEQ ID NO:11:

```
AAAGAACCGC TATGTCAGTC TGACGGCCCA GGCCTTTATG GAACTAAGCC GGGAAAGTCT    60

TAAACAAACG TTTGATGAAG GCTGTCTGGG AAACAAAGAT GAAATATTT AGAAAACAAA   120

GACGAAACGT GGTAGTATAG GAATACAAAC TAAATCTTAT AAAACAAAGG GGAATAATCG   180

GAA ATG CAA CTA TTC GAT CTG CCG CTC GAC CAA TTG CAA ACA TAT AAG    228
    Met Gln Leu Phe Asp Leu Pro Leu Asp Gln Leu Gln Thr Tyr Lys
    1               5                   10                  15

CCT GAA AAA ACA GCA CCG AAA GAT TTT TCT GAG TTT TGG AAA TTG TCT    276
```

|  |  |  |  |  |  |  |  |  |  |  |  |  |  |  |  |
|---|---|---|---|---|---|---|---|---|---|---|---|---|---|---|---|
| Pro | Glu | Lys | Thr | Ala | Pro | Lys | Asp | Phe | Ser | Glu | Phe | Trp | Lys | Leu | Ser |
|  |  |  | 20 |  |  |  |  | 25 |  |  |  |  | 30 |  |  |

```
TTG GAG GAA CTT GCA AAA GTC CAA GCA GAA CCT GAT CTA CAG CCG GTT      324
Leu Glu Glu Leu Ala Lys Val Gln Ala Glu Pro Asp Leu Gln Pro Val
            35                  40                  45

GAC TAT CCT GCT GAC GGA GTA AAA GTG TAC CGT CTC ACA TAT AAA AGC      372
Asp Tyr Pro Ala Asp Gly Val Lys Val Tyr Arg Leu Thr Tyr Lys Ser
        50                  55                  60

TTC GGA AAC GCC CGC ATT ACC GGA TGG TAC GCG GTG CCT GAC AAG CAA      420
Phe Gly Asn Ala Arg Ile Thr Gly Trp Tyr Ala Val Pro Asp Lys Gln
65                  70                  75

GGC CCG CAT CCG GCG ATC GTG AAA TAT CAT GGC TAC AAT GCA AGC TAT      468
Gly Pro His Pro Ala Ile Val Lys Tyr His Gly Tyr Asn Ala Ser Tyr
80                  85                  90                  95

GAT GGT GAG ATT CAT GAA ATG GTA AAC TGG GCA CTC CAT GGC TAC GCC      516
Asp Gly Glu Ile His Glu Met Val Asn Trp Ala Leu His Gly Tyr Ala
                100                 105                 110

GCA TTC GGC ATG CTT GTC CGC GGC CAG CAG AGC AGC GAG GAT ACG AGT      564
Ala Phe Gly Met Leu Val Arg Gly Gln Gln Ser Ser Glu Asp Thr Ser
            115                 120                 125

ATT TCA CTG CAC GGT CAT GCT TTG GGC TGG ATG ACG AAA GGA ATT CTT      612
Ile Ser Leu His Gly His Ala Leu Gly Trp Met Thr Lys Gly Ile Leu
        130                 135                 140

GAT AAA GAT ACA TAC TAT TAC CGC GGT GTT TAT TTG GAC GCC GTC CGC      660
Asp Lys Asp Thr Tyr Tyr Tyr Arg Gly Val Tyr Leu Asp Ala Val Arg
145                 150                 155

GCG CTT GAG GTC ATC AGC AGC TTC GAC GAG GTT GAC GAA ACA AGG ATC      708
Ala Leu Glu Val Ile Ser Ser Phe Asp Glu Val Asp Glu Thr Arg Ile
160                 165                 170                 175

GGT GTG ACA GGA GGA AGC CAA GGC GGA GGT TTA ACC ATT GCC GCA GCA      756
Gly Val Thr Gly Gly Ser Gln Gly Gly Gly Leu Thr Ile Ala Ala Ala
            180                 185                 190

GCG CTG TCA GAC ATT CCA AAA GCC GCG GTT GCC GAT TAT CCT TAT TTA      804
Ala Leu Ser Asp Ile Pro Lys Ala Ala Val Ala Asp Tyr Pro Tyr Leu
        195                 200                 205

AGC AAC TTC GAA CGG GCC ATT GAT GTG GCG CTT GAA CAG CCG TAC CTT      852
Ser Asn Phe Glu Arg Ala Ile Asp Val Ala Leu Glu Gln Pro Tyr Leu
            210                 215                 220

GAA ATC AAT TCC TTC TTC AGA AGA AAT GGC AGC CCG GAA ACA GAA GTG      900
Glu Ile Asn Ser Phe Phe Arg Arg Asn Gly Ser Pro Glu Thr Glu Val
        225                 230                 235

CAG GCG ATG AAG ACA CTT TCA TAT TTC GAT ATT ATG AAT CTC GCT GAC      948
Gln Ala Met Lys Thr Leu Ser Tyr Phe Asp Ile Met Asn Leu Ala Asp
240                 245                 250                 255

CGA GTG AAG GTG CCT GTC CTG ATG TCA ATC GGC CTG ATT GAC AAG GTC      996
Arg Val Lys Val Pro Val Leu Met Ser Ile Gly Leu Ile Asp Lys Val
            260                 265                 270

ACG CCG CCG TCC ACC GTG TTT GCC GCC TAC AAT CAT TTG GAA ACA GAG     1044
Thr Pro Pro Ser Thr Val Phe Ala Ala Tyr Asn His Leu Glu Thr Glu
        275                 280                 285

AAA GAG CTG AAG GTG TAC CGC TAC TTC GGA CAT GAG TAT ATC CCT GCT     1092
Lys Glu Leu Lys Val Tyr Arg Tyr Phe Gly His Glu Tyr Ile Pro Ala
            290                 295                 300

TTT CAA ACG GAA AAA CTT GCT TTC TTT AAG CAG CAT CTT AAA GGC TGA     1140
Phe Gln Thr Glu Lys Leu Ala Phe Phe Lys Gln His Leu Lys Gly
305                 310                 315

TAAATGTGAA AAGCCGCCGC ATATCATCAG GCGGTTTTTT TCTGCAAACT GCCGGAATGA  1200

GAACAGACTG GAGACGAATA GATATGAAAC AAAGAATCAT TAATGAATTA AAACGGATCG  1260

AGCAGTCATA CGGAGTCAAA ATCGTGTATG CCGTCGAGTC AGGAAGCCGC GCATGGGGAT  1320

TTCCCTCGCA GGATAGTGAT TACGACGTCC GCTTTATTTA TGTGCCGAAA AAGGAGTGGT  1380
```

-continued

```
ACTTTTCAAT TGAGCAGGAG CGTGATGTCA TTGAGGAACC GATTCACGAT TTGCTGGATA 1440
TCAGCGGCTG GGAGCTGAGA AAAACGCTTC GGCTTTTCAA AAAGTCAAAC CCTCCGCTCC 1500
TCGAATGGCT GTCCTCAGAC ATTGTGTATT ACGAAGCATT TACGACCGCA GAGCAGTTAA 1560
GAAAACTGCG CACGGAGGCA TTTAAGCCTG AAGCAAGCGT GTATCACTAT ATCAATATGG 1620
CGAGAAGGAA CGTCAAAGAT TATCTACAAG GACAAGAGGT CAAAATTAAA AAGTACTTCT 1680
ACGTTCTTCG GCCTATTTTG GCTGCAATGG ATTGAAAGCA CGGAACCATA CCGCCAATGG 1740
ACTTTACTGT TTTGATGAAT GAACTTGTTG CTGAACCCGA GCTGAAGGCT GAAATGGAAA 1800
CCTTGCTTGA ACGGAAAAGA AGAGGGGAAG AGATTGACCT CGAATCAAAG AACTGATGTA 1860
ATTCACCAAT TCATTGAAAC GGAAATCGAA AGAATCATGG AAGCACAAAA AGAACTGAAG 1920
GCAGAGAAAA AAGATATGAC ATCTGAATTG AACCGTTTAC TTTTGAATAC GGTTGAAGAA 1980
GTGTGGAAGG ATGGAGGAAG CTGATGTTTT TTGTCGCTTC CTTTCTCCT  TTATTCGACA 2040
GAATTC                                                          2046
```

What is claimed is:

1. A purified protein having the amino acid sequence of Sequence I.D. No. 1.

2. A purified protein having the amino acid sequence further containing methionine at the amino-terminus of the amino acid sequence of Sequence I.D. No. 1.

3. The protein according to claim 1 produced by an *Escherichia coli* cell transformed with a recombinant DNA molecule prepared by introducing a DNA base sequence encoding the amino acid sequence of Sequence I.D. No. 1 into a vector used in an *E. coli* host-vector system.

4. The protein according to claim 2 produced by an *Escherichia coli* cell transformed with a recombinant DNA molecule prepared by introducing a DNA base sequence encoding the amino acid sequence of Sequence I.D. No. 1 into a vector used in an *E. coli* host-vector system.

5. A purified enzyme composed of a multimer of the protein of claim 1.

6. A purified enzyme composed of a multimer of the protein of claim 2.

7. A purified enzyme composed of a multimer of the protein of claim 3.

8. A purified enzyme composed of a multimer of the protein of claim 4.

9. The purified enzyme according to claim 5 which is a tetramer or octamer of said protein.

10. The purified enzyme according to claim 6 which is a tetramer or octamer of said protein.

11. The purified enzyme according to claim 7 which is a tetramer or octamer of said protein.

12. The purified enzyme according to claim 8 which is a tetramer or octamer of said protein.

* * * * *

UNITED STATES PATENT AND TRADEMARK OFFICE
CERTIFICATE OF CORRECTION

PATENT NO. : 5,338,676
DATED : August 16, 1994
INVENTOR(S) : Mitsushima et al.

It is certified that error appears in the above-identified patent and that said Letters Patent is hereby corrected as shown below:

On the title page, item [75], change "Yaqi" to --Yagi--.

Signed and Sealed this

Fourth Day of October, 1994

Attest:

BRUCE LEHMAN

Attesting Officer          Commissioner of Patents and Trademarks